(12) United States Patent
Kuang et al.

(10) Patent No.: US 10,980,441 B2
(45) Date of Patent: Apr. 20, 2021

(54) PROTOCOL PARAMETER SELECTION METHOD, APPARATUS AND MAGNETIC RESONANCE IMAGING SYSTEM

(71) Applicant: Siemens Healthcare GmbH, Erlangen (DE)

(72) Inventors: Bin Kuang, Shenzhen (CN); Le Zhang, Shenzhen (CN); Liu En Yang, Shenzhen (CN)

(73) Assignee: Siemens Healthcare GmbH, Erlangen (DE)

( * ) Notice: Subject to any disclaimer, the term of this patent is extended or adjusted under 35 U.S.C. 154(b) by 74 days.

(21) Appl. No.: 16/531,483

(22) Filed: Aug. 5, 2019

(65) Prior Publication Data
US 2020/0037919 A1 Feb. 6, 2020

(30) Foreign Application Priority Data
Aug. 6, 2018 (CN) .......................... 201810885611.7

(51) Int. Cl.
| | | |
|---|---|---|
| *G01V 3/00* | (2006.01) | |
| *A61B 5/055* | (2006.01) | |
| *G01R 33/56* | (2006.01) | |
| *G01R 33/385* | (2006.01) | |
| *G01R 33/561* | (2006.01) | |
| *G01R 33/565* | (2006.01) | |
| *G06T 7/00* | (2017.01) | |
| *G01R 33/54* | (2006.01) | |
| *G01R 33/3415* | (2006.01) | |

(52) U.S. Cl.
CPC ............ *A61B 5/055* (2013.01); *G01R 33/385* (2013.01); *G01R 33/5608* (2013.01); *G01R 33/3415* (2013.01); *G01R 33/543* (2013.01); *G01R 33/5601* (2013.01); *G01R 33/5611* (2013.01); *G01R 33/56509* (2013.01); *G06T 7/0012* (2013.01); *G06T 2207/10088* (2013.01)

(58) Field of Classification Search
CPC .............. G01R 33/543; G01R 33/5659; G01R 33/3415; G01R 33/36; A61B 5/055
USPC ........................................................ 324/309
See application file for complete search history.

*Primary Examiner* — Walter L Lindsay, Jr.
*Assistant Examiner* — Frederick Wenderoth
(74) *Attorney, Agent, or Firm* — Schiff Hardin LLP

(57) ABSTRACT

In a protocol parameter selection method and corresponding device, when previewing a current sequence in multiple predetermined sequences, a corresponding reference performance index radar chart is displayed in a standard radar chart, according to a reference value of each performance index in multiple performance indices obtained in advance on the basis of the current sequence. The standard radar chart is a radar chart generated using the multiple performance indices as components and using as a standard a standard value of each performance index obtained in advance on the basis of at least one sequence. The method and device also include determining, as a sequence required for scanning, a current sequence selected according to the reference performance index radar chart and a performance index currently of interest.

18 Claims, 4 Drawing Sheets

PROTOCOL PARAMETER SELECTION METHOD, APPARATUS AND MAGNETIC RESONANCE IMAGING SYSTEM

CROSS REFERENCE TO RELATED APPLICATIONS

This patent application claims priority to Chinese Patent Application No. 201810885611.7, filed Aug. 6, 2018, which is incorporated herein by reference in its entirety.

BACKGROUND

Field

The present disclosure relates to the technical field of magnetic resonance imaging systems, in particular to a protocol parameter selection method for a magnetic resonance imaging system, an apparatus and a magnetic resonance imaging system.

Related Art

Magnetic resonance imaging (MRI) is a technology in which the phenomenon of magnetic resonance is used to perform imaging. In an MRI system, a very large number of protocols and protocol parameters such as sequences are designed; this makes it very difficult for an inexperienced user to select therefrom the sequence and protocol needed for the current scan. Furthermore, for each sequence, there is a very large number of adjustable parameters, such as layer thickness, field of view in the phase encoding direction ($FOV_{PE}$), field of view in the readout direction ($FOV_{RO}$), number of phase encoding steps ($N_{PE}$), resolution in readout direction ($N_{RO}$), number of scan repetitions ($N_{AVE}$), bandwidth, phase encoding overlap rate (Phase Over), flip angle, magnetization vector transfer (MTC) and parallel imaging (iPAT) etc.; when different sequences and parameters are selected, it is possible that different MRI performances will be obtained, e.g. signal to noise ratio (SNR), scan time (ST), contrast ratio (CR), resolution (Res), fat suppression (Fat Sat), etc., and a novice user will generally be unable to understand the nature of the MRI performances corresponding to different sequences and parameters, and will therefore find it very difficult to obtain a protocol with balanced performance that meets scanning requirements.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
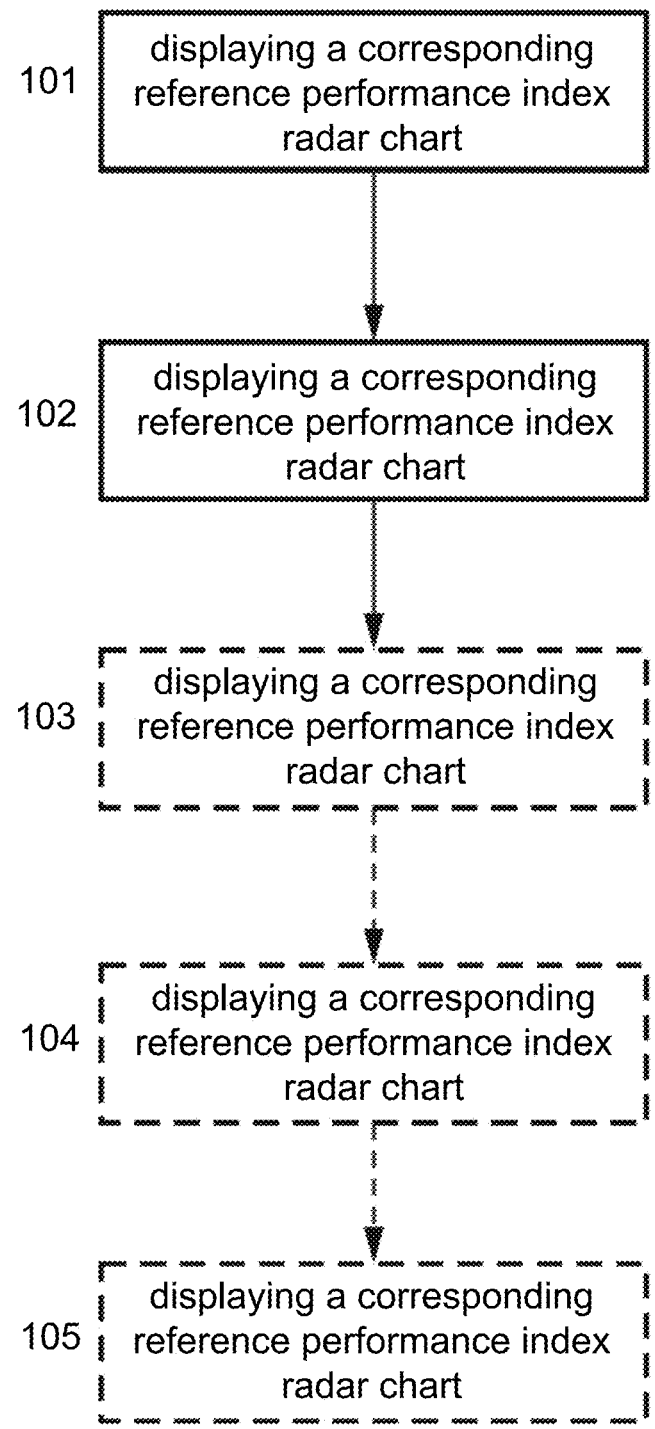
FIG. 1 is a flow chart of a sequence selection method for an MRI system according to an exemplary embodiment of the present disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

Exemplary embodiments of the present disclosure are directed to a protocol parameter selection method for an MRI system, a protocol parameter selection apparatus for an MRI system, and an MRI system, which are used to display, in a visually direct manner, states and dynamic balance situations of scanning performances of the MRI system corresponding to different protocol parameters, to facilitate the selection of protocol parameters. Advantageously, exemplary embodiments of the present disclosure provide displaying, in a visually direct manner, states and dynamic balance situations of scanning performances of the MRI system corresponding to different protocol parameters, so that the selection of protocol parameters can be performed conveniently.

A protocol parameter selection method for an MRI system according to an exemplary embodiment includes: when previewing a current sequence in multiple predetermined sequences, displaying a corresponding reference performance index radar chart in a standard radar chart, according to a reference value of each performance index in multiple performance indices obtained in advance on the basis of the current sequence. The standard radar chart is a radar chart generated using the multiple performance indices as components and using as a standard a standard value of each performance index obtained in advance on the basis of at least one sequence. The method can also include determining, as a sequence required for scanning, a current sequence selected according to the reference performance index radar chart and a performance index currently of interest.

In an exemplary embodiment, when previewing a current parameter of the current sequence, obtaining current values of the multiple performance indices according to the current parameter; generating and displaying a corresponding current performance index radar chart in the standard radar chart according to the current values of the multiple performance indices; determining, as a parameter required for scanning, the current parameter selected according to the current performance index radar chart and a performance index currently of interest.

In an exemplary embodiment, the method may further include: when adjusting and previewing a parameter of the current sequence, determining a parameter change amount, relative to a previous parameter, of the current parameter obtained by adjustment; determining performance index change amounts of the current values of the multiple performance indices corresponding to the current parameter, relative to previous values of the multiple performance indices, according to the parameter change amount; generating and displaying the corresponding current performance index radar chart in the standard radar chart according to the performance index change amount.

In an exemplary embodiment, the standard radar chart normalizes the standard value of each of the performance indices to be a set value for display; the step of displaying the corresponding reference performance index radar chart in the standard radar chart, according to the reference value of each performance index in the multiple performance indices obtained in advance on the basis of the current sequence, includes: normalizing the reference value of each performance index in the multiple performance indices obtained in advance on the basis of the current sequence, based on the standard value of each of the performance indices and the set value, and displaying the corresponding reference performance index radar chart in the standard radar chart according to a normalized performance index value; the step of generating and displaying the corresponding current performance index radar chart in the standard radar chart, according to the current values of the multiple performance indices, includes: normalizing the current values of the multiple performance indices, based on the standard value of each of the performance indices and the set value, and generating and displaying the corresponding current performance index radar chart in the standard radar chart according to the normalized performance index value.

In an exemplary embodiment, the reference value of each performance index in the multiple performance indices obtained in advance on the basis of the current sequence is: a maximum value of each performance index obtained by performing parameter adjustment on the basis of the current sequence; or a value of each performance index obtained on the basis of a set of recommended parameters of the current sequence.

In an exemplary embodiment, the standard value of each performance index obtained in advance on the basis of at least one sequence is: a maximum value of each performance index obtained by performing parameter adjustment on the basis of a single sequence; or a value of each performance index obtained on the basis of a set of recommended parameters of a single sequence; or a maximum value of each performance index obtained by performing parameter adjustment on the basis of multiple sequences.

In an exemplary embodiment, the method further includes: determining an advance warning value of each performance index in advance; and when previewing the current parameter of the current sequence, further includes: displaying a corresponding advance warning performance index radar chart in the standard radar chart according to the advance warning value of each of the performance indices.

In an exemplary embodiment, the method further includes: setting in advance a default recommended parameter corresponding to each scanning region for each sequence in the multiple sequences, and obtaining a recommended value of each performance index to correspond to the recommended parameter; the recommended parameter enabling each performance index to attain a set balance on the basis of the current sequence; and when previewing the current parameter of the current sequence, further includes: displaying a corresponding recommended performance index radar chart in the standard radar chart according to the recommended value of each of the performance indices.

A protocol parameter selection apparatus for an MRI system proposed in an embodiment of the present disclosure includes: a radar chart display which, when previewing a current sequence in multiple predetermined sequences, displays a corresponding reference performance index radar chart in a standard radar chart, according to a reference value of each performance index in multiple performance indices obtained in advance on the basis of the sequence, wherein the standard radar chart is a radar chart generated using the multiple performance indices as components and using as a standard a standard value of each performance index obtained in advance on the basis of at least one sequence; and a sequence determiner which determines, as a sequence required for scanning, the current sequence selected according to the reference performance index radar chart and a performance index currently of interest.

In an exemplary embodiment, the apparatus further includes: a performance index value determiner and a parameter determiner, wherein the performance index value determiner obtains, when previewing a current parameter of the current sequence, current values of the multiple performance indices according to the current parameter; the radar chart display further generates and displays a corresponding current performance index radar chart in the standard radar chart according to the current values of the multiple performance indices; the parameter determiner determines, as a parameter required for scanning, the current parameter selected according to the current performance index radar chart and a performance index currently of interest.

In an exemplary embodiment, the apparatus further includes: a parameter change amount determiner which determines, when adjusting and previewing a parameter of the current sequence, a parameter change amount of the current parameter relative to a previous parameter; a performance index change amount determiner, which determines performance index change amounts of the current values of the multiple performance indices corresponding to the current parameter, relative to previous values of the multiple performance indices, according to the parameter change amount; the radar chart display generator generating and displaying the corresponding current performance index radar chart in the standard radar chart according to the performance index change amounts.

In an exemplary embodiment, the standard radar chart normalizes the standard value of each of the performance indices to be a set value for display; when previewing the current sequence in the multiple predetermined sequences, the radar chart display generator normalizes the reference value of each performance index in the multiple performance indices obtained in advance on the basis of the sequence, based on the standard value of each of the performance indices and the set value, and displays the corresponding reference performance index radar chart in the standard radar chart according to a normalized performance index value; and when previewing the current parameter of the current sequence, normalizes the current values of the multiple performance indices on the basis of the standard value of each of the performance indices and the set value, and generates and displays the corresponding current performance index radar chart in the standard radar chart according to the normalized performance index value.

In an exemplary embodiment, the apparatus further includes: a storage, which stores the reference value of each performance index in the multiple performance indices obtained in advance on the basis of the current sequence, wherein the reference value of each performance index in the multiple performance indices obtained in advance on the basis of the current sequence is: a maximum value of each performance index obtained by performing parameter adjustment on the basis of the current sequence; or a value of each performance index obtained on the basis of a set of recommended parameters of the current sequence.

In an exemplary embodiment, the storage further stores the standard value of each performance index obtained in advance on the basis of at least one sequence, wherein the standard value of each performance index obtained in advance on the basis of at least one sequence is: a maximum value of each performance index obtained by performing parameter adjustment on the basis of a single sequence; or a value of each performance index obtained on the basis of a set of recommended parameters of a single sequence; or a maximum value of each performance index obtained by performing parameter adjustment on the basis of multiple sequences.

In an exemplary embodiment, the storage further stores an advance warning value of each performance index; when previewing the current parameter of the current sequence, the radar chart display generator further displays a corresponding advance warning performance index radar chart in the standard radar chart according to the advance warning value of each of the performance indices.

In an exemplary embodiment, the storage further stores a default recommended parameter, corresponding to each scanning region, which is set in advance for each sequence in the multiple sequences, and a recommended value of each performance index obtained to correspond to the recommended parameter; the recommended parameter enabling each performance index to attain a set balance on the basis of the current sequence; when previewing the current parameter of the current sequence, the radar chart display generator further displays a corresponding recommended performance index radar chart in the standard radar chart according to the recommended value of each of the performance indices.

Another protocol parameter selection apparatus for an MRI system proposed in an embodiment of the present disclosure includes: at least one memory and at least one processor, wherein: the at least one memory stores a computer program; the at least one processor calls the computer program stored in the at least one memory, and performs the protocol parameter selection method for an MRI system as described in any one of the embodiments above.

In an exemplary embodiment, an MRI system proposed in an embodiment of the present disclosure includes: the protocol parameter selection apparatus as described in one or more of the embodiments described herein.

In an exemplary embodiment, a computer-readable storage medium includes a computer program stored thereon; the computer program is executable by a processor and realizes the protocol parameter selection method as described in one or more of the exemplary embodiments described herein.

Clearly, in embodiments of the present disclosure, through the use of performance index radar charts, when different sequences are being selected, states and dynamic balance situations of scanning performances of the MRI system corresponding to different sequences are displayed in a visually direct manner in a standard radar chart, so that sequence selection can be performed conveniently. Furthermore, when different parameters are being selected under the current sequence, states and dynamic balance situations of scanning performances of the MRI system corresponding to different parameters under the current sequence are displayed in a visually direct manner in the standard radar chart, so the selection of parameters under the current sequence can be performed conveniently.

Furthermore, when adjusting and previewing a parameter of the current sequence, a corresponding performance index change amount is determined quickly according to a change amount of a parameter currently awaiting adjustment, thereby quickly realizing the adjustment of the current performance index radar chart, and thereby improving the efficiency of parameter adjustment.

Furthermore, by displaying in a normalized manner the standard value, reference value and current value of each performance index, it is possible to make the characteristics of the performance index more obvious correspondingly under different sequences and parameters, thereby further facilitating the selection of different sequences and parameters.

Furthermore, in this embodiment, many methods of setting the performance index reference value and the performance index standard value are possible, so implementation is flexible.

Furthermore, displaying the corresponding advance warning performance index radar chart in the standard radar chart according to an advance warning value of each performance index when a user is performing parameter adjustment can make it easier for the user to understand the optimal adjustment range of the parameter, to avoid a situation where a poor performance index is obtained after parameter adjustment; this is extremely beneficial for novice users.

Furthermore, the displaying, on the standard radar chart, of the recommended value of each performance index obtained according to the default recommended parameter when a user is performing parameter adjustment can help the user, in particular the novice user, to select a better parameter, i.e. the user can perform fine adjustment of the parameter according to the recommended performance index radar chart corresponding to the recommended parameter, to obtain the parameter satisfying the performance required thereby.

In embodiments of the present disclosure, in order to make it easy for a user to perform sequence selection and parameter selection under a certain sequence, consideration is given to the provision, for the user, of a visually direct display of scanning performance of an MRI system corresponding to different sequences and parameters under a certain sequence. For this purpose, a scanning performance radar chart with various performance indices as components is designed, in order to display in a visually direct manner the scanning performance tendencies and characteristics of different sequences, as well as changes in performance among different parameters under the same sequence, so that the user can select a sequence suitable for him/herself and parameters under the sequence according to his/her own needs regarding certain performances, based on the intuitively visualized scanning performance radar chart, on condition that this is permitted by a current hardware system. Furthermore, it is also possible to display, on the scanning performance radar chart, a recommended performance radar chart corresponding to a set of default recommended parameters corresponding to a current scanning region under the sequence, to facilitate the rapid acquisition of an optimal configuration of scanning parameters by a novice user, and the efficiency with which a novice user learns parameter adjustment and sequence selection is accelerated.

FIG. 1 is a demonstrative flow chart of a sequence selection method for an MRI system in an embodiment of the present disclosure. As FIG. 1 shows, in an exemplary embodiment, the method includes the following steps:

Step 101, when previewing a current sequence in multiple predetermined sequences, displaying a corresponding reference performance index radar chart in a standard radar chart, according to a reference value of each performance index in multiple performance indices obtained in advance on the basis of the current sequence. The standard radar chart is a radar chart generated using the multiple performance indices as components and using as a standard a standard value of each performance index obtained in advance on the basis of at least one sequence.

In this step, multiple sequences may include purchased sequences supported by a current MRI system and sequences which can be further purchased; or may only include purchased sequences. An operation of previewing the current sequence can be realized by choosing each sequence. There are many types of sequences in the MRI system, e.g. GRE sequences, SE sequences, EPI sequences, etc.

A reference value of each performance index in multiple performance indices obtained in advance on the basis of the current sequence may be: a maximum value of each performance index obtained by performing parameter adjustment on the basis of the current sequence; and/or: a value of each performance index obtained on the basis of a set of recommended parameters of the current sequence. Recommended parameters may be different for different scanning regions.

A standard value of each performance index obtained in advance on the basis of at least one sequence may be: a maximum value of each performance index obtained by performing parameter adjustment on the basis of a single sequence; or a value of each performance index obtained on the basis of a set of recommended parameters of a single sequence; or a maximum value of each performance index obtained by performing parameter adjustment on the basis of multiple sequences.

Figure 2A:
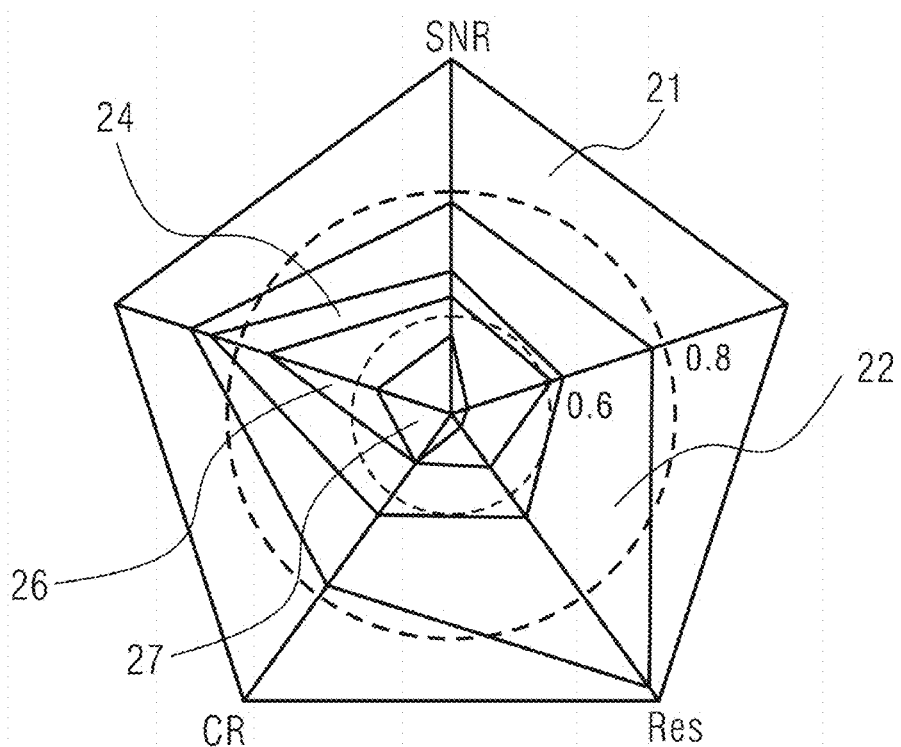
FIGS. 2A and 2B are schematic diagrams of radar charts of two sequences in a magnetic resonance system according to an exemplary embodiments of the present disclosure.
Figure 2B:
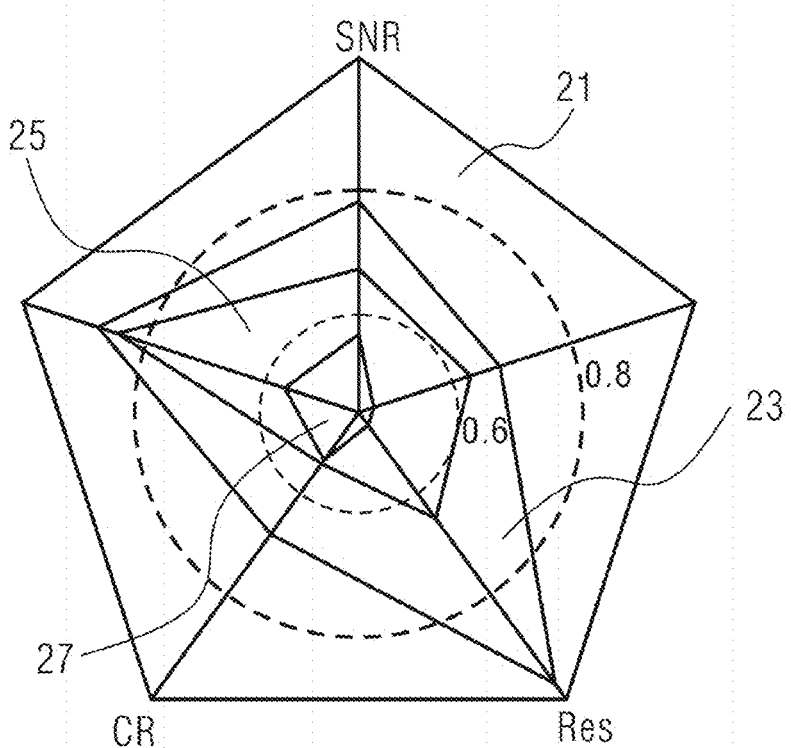

FIGS. 2A and 2B show schematic diagrams of radar charts of two sequences in a magnetic resonance system in an embodiment of the present disclosure. As shown in FIGS. 2A and 2B, five components of the radar chart in this embodiment are five performance indices, namely signal to noise ratio (SNR), scan time (ST), contrast ratio (CR), resolution (Res) and fat suppression (Fat Sat, FS), with an outermost regular pentagon 21 being a standard radar chart; the standard radar chart in this embodiment is obtained by using as a standard a maximum value of each performance index obtained by performing parameter adjustment on the basis of multiple sequences, and subjecting this to normalization. In this embodiment, the case where it is normalized to 1 is taken as an example; in other embodiments, it could also be normalized to another positive integer, such as 2, . . . , 5, . . . , 10, . . . , 20, etc. Next-outermost pentagons 22 and 23, and pentagons 24 and 25 located inside pentagons 22 and 23 respectively, are reference performance index radar charts formed by reference values of each performance index corresponding to two sequences respectively. In this embodiment, for each sequence, two reference performance index radar charts are set. Each performance index corresponding to pentagons 22 and 23 is a maximum value of each performance index obtained by performing parameter adjustment on the basis of the respective sequence. Each performance index corresponding to pentagons 24 and 25 is a value of each performance index obtained on the basis of a set of recommended parameters of the respective sequence. In other embodiments, there may be only one set of reference performance index radar charts.

When the reference performance index radar chart is generated, it is necessary to first of all normalize the reference value of each performance index obtained in advance on the basis of the current sequence, based on a standard value of each of the performance indices in the standard radar chart and the set value, and display a corresponding reference performance index radar chart in the standard radar chart according to the normalized performance index value.

Step 102 includes, determining, as a sequence required for scanning, a current sequence selected according to the reference performance index radar chart and a performance index currently of interest.

In this step, a sequence required for scanning may be selected according to an advantage of a performance index corresponding to each sequence and a performance index currently of interest. For example, a maximum adjustable range of the contrast ratio and fat suppression of the sequence corresponding to FIG. 2A is superior to the contrast ratio and fat suppression of the sequence corresponding to FIG. 2B. If contrast ratio and/or fat suppression are currently being followed with relative interest, then the sequence corresponding to FIG. 2A can be selected.

Through the use, as described above, of performance index radar charts corresponding to different sequences to display in a visually direct manner scanning performance tendencies and characteristics of different sequences, a user is enabled to select a sequence suitable for him/herself according to his/her own needs regarding certain performances, on condition that this is permitted by a current hardware system.

Once the sequence selection described above has been completed, other embodiments may further include performing a step of selecting a parameter under a selected sequence as described below, as shown by the dotted-line part in FIG. 1.

Step 103, when previewing a certain set of parameters (for convenience of description, referred to as current parameters herein below) of a selected sequence (for convenience of description, referred to as a current sequence herein below), obtaining current values of multiple performance indices according to the parameters.

Since the values of each performance index corresponding to different parameters are generally different, a performance index value corresponding to the parameter must be determined when different parameters are browsed.

Step 104, generating and displaying a corresponding current performance index radar chart in the standard radar chart according to the current values of the multiple performance indices.

In this step, still taking the case of the two sequences corresponding to FIGS. 2A and 2B as an example, supposing the selected current sequence is the sequence corresponding to FIG. 2A, then the current values of the multiple performance indices can first of all be normalized on the basis of the standard value of each of the performance indices and the set value, and a current performance index radar chart corresponding to pentagon 26 can be generated and displayed in the standard radar chart according to the normalized performance index values.

In order to avoid a situation where a poor performance index is obtained in the process of parameter selection, in an embodiment of the present disclosure, an advance warning value of each performance index can be further determined in advance; then in step 103, an advance warning performance index radar chart as shown by pentagon 27 can further be displayed in the standard radar chart according to the advance warning value of each of the performance indices.

Furthermore, if the reference performance index radar chart in step 101 does not include a performance index radar chart corresponding to a default recommended parameter as shown by pentagons 24 and 25, in an embodiment of the present disclosure, a default recommended parameter corresponding to each scanning region can further be set in advance for each sequence in the multiple sequences, and a recommended value of each performance index can be obtained to correspond to the recommended parameter; the recommended parameter enables each performance index to attain a set balance on the basis of the current sequence. Correspondingly, in step 103, a recommended performance index radar chart as shown by pentagons 24 and 25 can be further displayed in the standard radar chart, according to the recommended value of each of the performance indices, when previewing a current parameter of a current sequence.

Furthermore, in order to facilitate parameter adjustment in the process of parameter selection, in an embodiment of the present disclosure, a correspondence relationship between a parameter change amount and a performance index change amount can be further set.

For example, taking a GRE sequence as an example, table 1 shows a table of a correspondence relationship between parameter change amounts and performance index change amounts under this sequence.

TABLE 1

| Parameter | Performance index | | | | |
| --- | --- | --- | --- | --- | --- |
| | SNR | CR | ST | RES | FS |
| layer thickness | 2 | 1 | 1 | 1 | 1 |
| $FOV_{PE}$ | 2 | 1 | 0.5 | 0.5 | ... |
| $FOV_{RO}$ | 2 | 1 | 1 | 0.5 | ... |
| $N_{PE}$ | $\sqrt{0.5}$ | 1 | $\sqrt{0.5}$ | 2 | ... |
| $N_{RO}$ | $\sqrt{0.5}$ | 1 | 1 | 2 | ... |
| $N_{ave}$ | ... | ... | ... | ... | ... |
| bandwidth | ... | ... | ... | ... | ... |
| phase encoding overlap rate | ... | ... | ... | ... | ... |
| flip angle | ... | ... | ... | ... | ... |
| MTC | ... | ... | ... | ... | ... |
| iPAT | ... | ... | ... | ... | ... |

Table 1 above only shows a portion of values; table 1 is now explained, taking the first line as an example. The data in the first line shows that when the layer thickness on the left side is doubled, the SNR in the performance indices is doubled, but CR, ST, RES and FS remain unchanged.

Based on the correspondence relationship, an embodiment of the present disclosure further includes: when adjusting and previewing a parameter of a current sequence, i.e. when a performance index radar chart corresponding to a previous parameter exists, determining a parameter change amount of a current parameter relative to the previous parameter, such as a change amount of layer thickness in table 1; determining performance index change amounts of current values of multiple performance indices corresponding to the current parameter, relative to previous values of the multiple performance indices, according to the parameter change amount, such as change amounts of SNR, CR, ST, RES and FS in table 1; then a corresponding current performance index radar chart can be generated and displayed in the standard radar chart according to the performance index change amounts, i.e. pentagon 26 shown in FIG. 2A can be adjusted directly according to the performance index change amounts. This process is simpler and quicker than the process of calculating a current value of each performance index according to a current parameter, and then normalizing the current value of each performance index according to a standard value of each performance index and a set value.

Step 105, determining, as a parameter required for scanning, a current parameter selected according to the current performance index radar chart and a performance index currently of interest.

Clearly, a scanning performance radar chart with various performance indices as components is designed in order to provide a visually direct display of scanning performance of an MRI system corresponding to different sequences and parameters under a certain sequence, so that a user can select a sequence suitable for him/herself and parameters under the sequence according to his/her own needs regarding certain performances, on condition that this is permitted by a current hardware system. Furthermore, by displaying, on the scanning performance radar chart, a recommended performance radar chart corresponding to a set of default recommended parameters corresponding to a current scanning region under the sequence, rapid acquisition of an optimal configuration of scanning parameters by a novice user can be facilitated, and the efficiency with which a novice user learns parameter adjustment and sequence selection is accelerated.

A protocol parameter selection method for an MRI system in embodiments of the present disclosure has been described in detail above; a protocol parameter selection apparatus for an MRI system in embodiments of the present disclosure is described in detail below. The apparatus in embodiments of the present disclosure may be used to realize the method in embodiments of the present disclosure; for details not disclosed in the apparatus embodiments, the corresponding descriptions in the method embodiments may be referred to.

Figure 3:
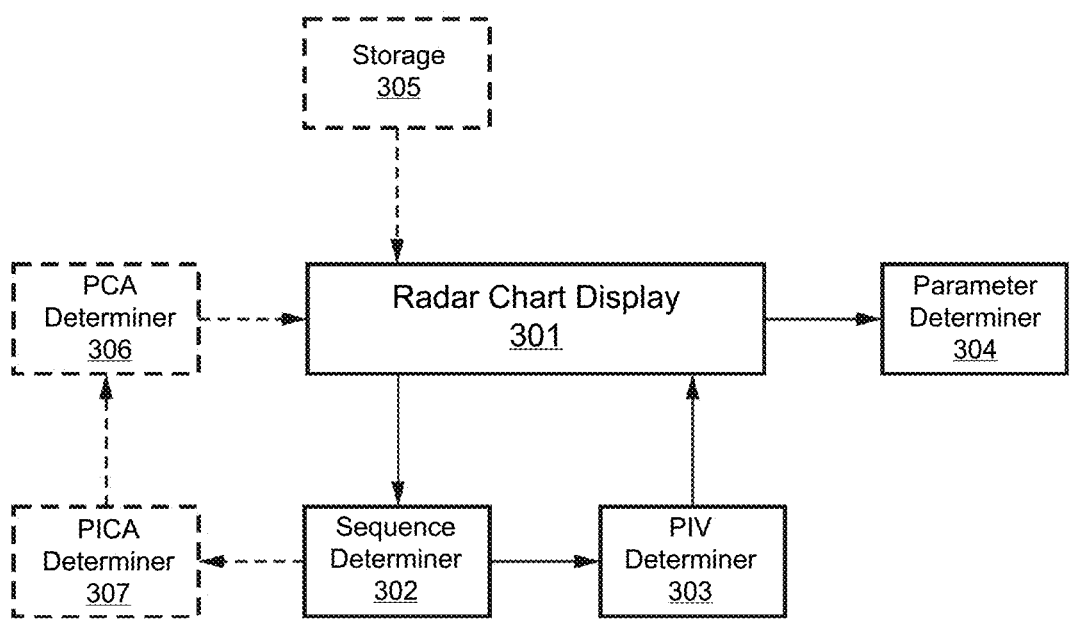
FIG. 3 is a structural schematic diagram of a protocol parameter selection apparatus for an MRI system according to an exemplary embodiments of the present disclosure.

FIG. 3 is a structural schematic diagram of a protocol parameter selection apparatus for an MRI system in an embodiment of the present disclosure. As shown in FIG. 3, in an exemplary embodiment, the apparatus includes: a radar chart display generator 301, a sequence determiner 302, a performance index value (PIV) determiner 303 and a parameter determiner 304. In some embodiments in which only sequence selection is performed, the apparatus may only include the radar chart display generator 301 and the sequence determiner 302. In an exemplary embodiment, the radar chart display generator 301, sequence determiner 302, performance index value (PIV) determiner 303 and parameter determiner 304 include processor circuitry that is configured to perform one or more respective functions/operations. In this example, the radar chart display generator 301, sequence determiner 302, performance index value (PIV) determiner 303 and parameter determiner 304 can be components of a processor. In another aspect, the radar chart display generator 301, sequence determiner 302, performance index value (PIV) determiner 303 and parameter determiner 304 are computer program modules that are stored (externally from the processor and/or internally in the processor), and when such computer programs are executed by the processor, cause the processor to perform the respective functions of the computer program modules.

In an exemplary embodiment, the radar chart display generator 301 is configured to generate a display signal of, when previewing a current sequence in multiple predetermined sequences, a corresponding reference performance index radar chart in a standard radar chart, according to a reference value of each performance index in multiple performance indices obtained in advance on the basis of the sequence.

The standard radar chart is a radar chart generated using the multiple performance indices as components and using as a standard a standard value of each performance index obtained in advance on the basis of at least one sequence. The multiple sequences may include: purchased sequences supported by a current MRI system and sequences which can be further purchased; or only include purchased sequences.

In an exemplary embodiment, the sequence determiner 302 is used for determining, as a sequence required for scanning, a current sequence selected according to the reference performance index radar chart and a performance index currently of interest.

In an exemplary embodiment, the performance index value determiner 303 is used for obtaining, when previewing a current parameter of a current sequence, current values of multiple performance indices according to the parameter.

In an exemplary embodiment, the radar chart display generator 301 further generates and displays a corresponding current performance index radar chart in the standard radar chart according to the current values of the multiple performance indices.

In an exemplary embodiment, the parameter determiner 304 is used for determining, as a parameter required for scanning, a current parameter selected according to the current performance index radar chart and a performance index currently of interest.

In an exemplary embodiment, the standard radar chart may normalize a standard value of each of the performance indices to be a set value for display; correspondingly, when previewing a current sequence in multiple predetermined sequences, the radar chart display generator 301 may normalize the reference value of each performance index in multiple performance indices obtained in advance on the basis of the sequence, based on the standard value of each of the performance indices and the set value, and display a corresponding reference performance index radar chart in the standard radar chart according to a normalized performance index value; and when previewing a current parameter of a current sequence, normalize the current values of the multiple performance indices on the basis of the standard value of each of the performance indices and the set value, and generate and display a corresponding current performance index radar chart in the standard radar chart according to the normalized performance index value.

In one or more embodiments, the apparatus may further include, as shown by the dotted-line part in FIG. 3: a storage 305, for storing the reference value of each performance index in multiple performance indices obtained in advance on the basis of a current sequence. The reference value of each performance index in multiple performance indices obtained in advance on the basis of a current sequence is: a maximum value of each performance index obtained by performing parameter adjustment on the basis of the current sequence; or a value of each performance index obtained on the basis of a set of recommended parameters of the current sequence.

Furthermore, the storage 305 may further store the standard value of each performance index obtained in advance on the basis of at least one sequence. The standard value of each performance index obtained in advance on the basis of at least one sequence may be: a maximum value of each performance index obtained by performing parameter adjustment on the basis of a single sequence; or a value of each performance index obtained on the basis of a set of recommended parameters of a single sequence; or a maximum value of each performance index obtained by performing parameter adjustment on the basis of multiple sequences.

In other embodiments, the apparatus may further include, as shown by the dotted-line part in FIG. 3: a parameter change amount determiner 306 and a performance index change amount determiner 307.

In an exemplary embodiment, the parameter change amount determiner 306 is used for determining, when a performance index radar chart corresponding to a previous parameter exists, a parameter change amount of a current parameter relative to the previous parameter.

In an exemplary embodiment, the performance index change amount determiner 307 is used for determining performance index change amounts of current values of multiple performance indices corresponding to the current parameter, relative to previous values of the multiple performance indices, according to the parameter change amount.

In an exemplary embodiment, the radar chart display generator 301 may generate and display a corresponding current performance index radar chart in the standard radar chart according to the performance index change amounts.

In other embodiments, the storage 305 may further store an advance warning value of each performance index determined in advance. Correspondingly, when previewing a current parameter of a current sequence, the radar chart display generator 301 may further display a corresponding advance warning performance index radar chart in the standard radar chart according to the advance warning value of each of the performance indices.

In one or more embodiments, the storage 305 may further store a default recommended parameter corresponding to each scanning region which is set in advance for each sequence in the multiple sequences, and a recommended value of each performance index obtained to correspond to the recommended parameter; the recommended parameter enables each performance index to attain a set balance on the basis of the current sequence. Correspondingly, when previewing a current parameter of a current sequence, the radar chart display generator 301 may further display a corresponding recommended performance index radar chart in the standard radar chart according to the recommended value of each of the performance indices.

Figure 4:
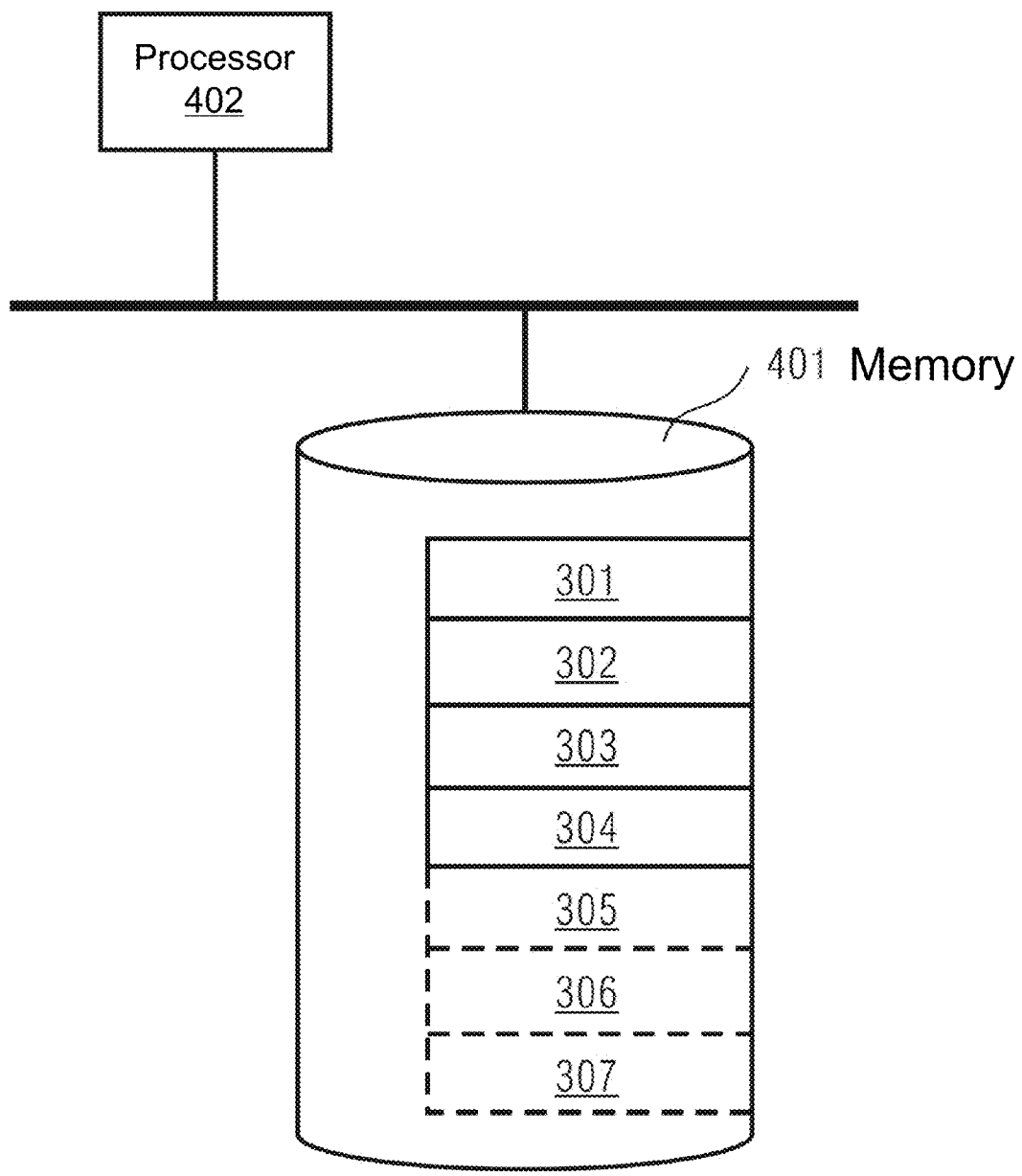
FIG. 4 is a structural diagram of another protocol parameter selection apparatus for an MRI system according to an exemplary embodiments of the present disclosure.

FIG. 4 is a protocol parameter selection apparatus, according to an embodiment, for an MRI system. As shown in FIG. 4, in an exemplary embodiment, the protocol parameter selection apparatus includes: at least one memory 401 and at least one processor 402. In an exemplary embodiment, the protocol parameter selection apparatus also includes one or more other components, such as communication ports, input/output ports, input devices (e.g. keyboard, mouse, etc.), output devices (display screen/monitor, speaker, etc.), etc. These components may communicate via a bus or other communication interfaces.

In an exemplary embodiment, the at least one memory 401 is used for storing data, including a computer program. In an exemplary embodiment, the memory 401 is any well-known volatile and/or non-volatile memory.

In an exemplary embodiment, the computer program includes various computer program modules of the protocol parameter selection apparatus shown in FIG. 3, i.e. the radar chart display generator 301, the sequence determiner 302, the performance index value determiner 303 and the parameter determiner 304. In other embodiments, the following may be further included: the storage 305, the parameter change amount (PCA) determiner 306 and the performance index change amount (PICA) determiner 307.

Furthermore, the at least one memory 401 may also store an operating system, etc. Operating systems include but are not limited to: an Android operating system, a Symbian operating system, a Windows operating system and a Linux operating system, etc.

In an exemplary embodiment, the at least one processor 402 is configured to call and execute the computer program stored in the at least one memory 401, in order to perform the protocol parameter selection method for an MRI system shown in FIG. 1, based on a function of at least one port receiving data. The processor 402 may be a CPU, a processing unit/module, an ASIC, a logic module or a programmable gate array, etc. In an exemplary embodiment, the processor 402 includes processor circuitry that is configured to perform one or more functions/operations of the processor 402, including performing one or more operations of a protocol parameter selection method according to aspects described herein.

Although FIG. 4 illustrates that the radar chart display generator 301, the sequence determiner 302, the performance index value determiner 303, the parameter determiner 304, the storage 305, the parameter change amount (PCA) determiner 306, and the performance index change amount (PICA) determiner 307 are stored externally from the processor 402, in one or more embodiments, one or more of these components may be internally stored within an internal memory of the processor 402. It should be further understood that one or more of the components 301-307 may be partially stored within memory 401 and partially stored in the internal memory of the processor 402.

In an embodiment of the present disclosure, an MRI system is provided, which may include the protocol parameter selection apparatus for an MRI system as shown in FIG. 3 or FIG. 4. As would be understood by one of ordinary skill in the art, the MRI system can include one or more conventional MRI system components, such as a magnetic resonance scanner that obtains MR image data from a person under examination. The magnetic resonance scanner can include a basic field magnet system, a gradient system, a RF transmit antenna system and a RF receive antenna system. The RF transmit antenna system can be a whole-body coil permanently installed in the magnetic resonance scanner.

In an exemplary embodiment, not all of the steps and modules in the flows and structural diagrams above are necessary; and certain steps or modules may be omitted according to actual requirements. The order in which steps are executed is not fixed, but may be adjusted as required. The partitioning of the modules is merely functional partitioning, employed for the purpose of facilitating description; during actual implementation, one module may be realized by multiple modules, and the functions of multiple modules may be realized by the same module; these modules may be located in the same device, or in different devices.

Hardware modules in the embodiments may be realized mechanically or electronically. For example, one hardware module may include a specially designed permanent circuit or logic device (such as a dedicated processor, such as an FPGA or ASIC) for completing a specific operation. The hardware module may also include a programmable logic device or circuit that is temporarily configured by software (e.g. comprising a general processor or another programmable processor) for executing a specific operation. The choice of whether to specifically use a mechanical method, or a dedicated permanent circuit, or a temporarily configured circuit (e.g. configured by software) to realize the hardware module can be decided according to considerations of cost and time.

The present disclosure also provides a machine-readable storage medium, in which is stored an instruction for causing a machine to execute the method according to the present application. Specifically, a system or apparatus equipped with a storage medium may be provided; software program code realizing the function of any one of the embodiments above is stored on the storage medium, and a computer (or CPU or MPU) of the system or apparatus is caused to read and execute the program code stored in the storage medium. Furthermore, it is also possible to cause an operating system etc. operating on a computer to complete a portion of, or all, actual operations by means of an instruction based on program code. It is also possible for program code read out from the storage medium to be written into a memory installed in an expansion board inserted in the computer, or written into a memory installed in an expansion unit connected to the computer, and thereafter instructions based on the program code cause a CPU etc. installed on the expansion board or expansion unit to execute a portion of and all actual operations, so as to realize the function of any one of the embodiments above. Embodiments of storage media used for providing program code include floppy disks, hard disks, magneto-optical disks, optical disks (such as CD-ROM, CD-R, CD-RW, DVD-ROM, DVD-RAM, DVD-RW, DVD+RW), magnetic tapes, non-volatile memory cards and ROM. Optionally, program code may be downloaded from a server computer via a communication network.

The embodiments above are merely preferred embodiments of the present disclosure, which are not intended to limit it. Any amendments, equivalent substitutions or improvements etc. made within the spirit and principles of the present disclosure shall be included in the scope of protection thereof.

The aforementioned description of the specific embodiments will so fully reveal the general nature of the disclosure that others can, by applying knowledge within the skill of the art, readily modify and/or adapt for various applications such specific embodiments, without undue experimentation, and without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computers, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, programmable processing circuit, other structural electronic hardware, or a combination thereof. A processor includes a microprocessor, a digital signal processor (DSP), central processing unit (CPU), application-specific instruction set processor (ASIP), graphics and/or image processor, multi-core processor, or other hardware processor. The processor may be "hardcoded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

REFERENCE LIST 101-105 method operations
21 standard radar chart
22, 23 reference performance index radar chart/maximum performance index radar chart
24, 25 reference performance index radar chart/recommended performance index radar chart
26, 27 current performance index radar chart
28 advance warning performance index radar chart
301 radar chart display generator
302 sequence determiner
303 performance index value determiner
304 parameter determiner
305 storage
306 parameter change amount determiner
307 performance index change amount determiner
401 memory
402 processor

The invention claimed is:

1. A protocol parameter selection method for a magnetic resonance imaging (MRI) system, comprising:
when previewing a current sequence of multiple predetermined sequences, displaying a corresponding reference performance index radar chart in a standard radar chart, according to a reference value of each performance index in multiple performance indices obtained in advance on the basis of the current sequence, wherein the standard radar chart is a radar chart generated using the multiple performance indices as components and using, as a standard, a standard value of each performance index obtained in advance based on at least one sequence; and
determining, as a sequence required for scanning, a current sequence selected based on the reference performance index radar chart and a performance index.

2. A protocol parameter selection apparatus for a magnetic resonance imaging (MRI) system, comprising:
a radar chart display generator, when previewing a current sequence in multiple predetermined sequences, is configured to display a corresponding reference performance index radar chart in a standard radar chart, according to a reference value of each performance index in multiple performance indices obtained in advance based on the sequence, wherein the standard radar chart is a radar chart generated using the multiple performance indices as components and using as a standard a standard value of each performance index obtained in advance based on at least one sequence; and
a sequencer configured to determine, as a sequence required for scanning, the current sequence selected based on the reference performance index radar chart and a performance index.

3. A non-transitory computer-readable storage medium, with a computer program stored thereon, that when executed by a processor, controls the processor to perform operations of a protocol parameter selection method for a magnetic resonance imaging (MRI) system, the operations comprising:
when previewing a current sequence of multiple predetermined sequences, displaying a corresponding reference performance index radar chart in a standard radar chart, according to a reference value of each performance index in multiple performance indices obtained in advance on the basis of the current sequence, wherein the standard radar chart is a radar chart generated using the multiple performance indices as components and using, as a standard, a standard value of each performance index obtained in advance based on at least one sequence; and
determining, as a sequence required for scanning, a current sequence selected based on the reference performance index radar chart and a performance index.

4. The method as claimed in claim 1, further comprising:
when previewing a current parameter of the current sequence, obtaining current values of the multiple performance indices based on the current parameter;
generating and displaying a corresponding current performance index radar chart in the standard radar chart based on the current values of the multiple performance indices; and determining, as a parameter required for scanning, the current parameter selected based on the current performance index radar chart and the performance index.

5. The method as claimed in claim 4, further comprising:
when adjusting and previewing a parameter of the current sequence, determining a parameter change amount, relative to a previous parameter, of the current parameter obtained by adjustment;
determining performance index change amounts of the current values of the multiple performance indices corresponding to the current parameter, relative to previous values of the multiple performance indices, based on the parameter change amount;
generating and displaying the corresponding current performance index radar chart in the standard radar chart based on the performance index change amount.

6. The method as claimed in claim 4, wherein:
the standard radar chart normalizes the standard value of each of the performance indices to be a set value for display;
the displaying the corresponding reference performance index radar chart in the standard radar chart comprises:
normalizing the reference value of each performance index in the multiple performance indices obtained in advance on the basis of the current sequence, based on the standard value of each of the performance indices and the set value, and
displaying the corresponding reference performance index radar chart in the standard radar chart based on a normalized performance index value; and
the generating and displaying the corresponding current performance index radar chart in the standard radar chart comprises:
normalizing the current values of the multiple performance indices, based on the standard value of each of the performance indices and the set value, and
generating and displaying the corresponding current performance index radar chart in the standard radar chart based on the normalized performance index value.

7. The method as claimed in claim 4, wherein the reference value of each performance index in the multiple performance indices comprises:
a maximum value of each performance index obtained by performing parameter adjustment based on the current sequence; or
a value of each performance index obtained based on a set of recommended parameters of the current sequence.

8. The method as claimed in claim 4, wherein the standard value of each performance index comprises:
a maximum value of each performance index obtained by performing parameter adjustment based on a single sequence;
a value of each performance index obtained based on a set of recommended parameters of the single sequence; or
a maximum value of each performance index obtained by performing parameter adjustment based on multiple sequences.

9. The method as claimed in claim 4, further comprising:
determining an advance warning value of each performance index in advance; and
when previewing the current parameter of the current sequence, displaying a corresponding advance warning performance index radar chart in the standard radar chart based on the advance warning value of each of the performance indices.

10. The method as claimed in claim 4, further comprising:
setting a default recommended parameter in advance corresponding to each scanning region for each sequence in the multiple sequences;
obtaining a recommended value of each performance index to correspond to the recommended parameter, the recommended parameter enabling each performance index to attain a set balance based on the current sequence; and
when previewing the current parameter of the current sequence, displaying a corresponding recommended performance index radar chart in the standard radar chart based on the recommended value of each of the performance indices.

11. The apparatus as claimed in claim 2, further comprising:
a performance index value calculator that is configured to obtain, when previewing a current parameter of the current sequence, current values of the multiple performance indices based on the current parameter, wherein the radar chart display generator is further configured to generate and display a corresponding current performance index radar chart in the standard radar chart based on the current values of the multiple performance indices; and
a parameter calculator that is configured to determine, as a parameter required for scanning, the current parameter selected based on the current performance index radar chart and the performance index.

12. The apparatus as claimed in claim 11, further comprising:
a parameter change amount calculator that is configured to, when adjusting and previewing a parameter of the current sequence, a parameter change amount of the current parameter relative to a previous parameter; and
a performance index change amount calculator that is configured to determine performance index change amounts of the current values of the multiple performance indices corresponding to the current parameter, relative to previous values of the multiple performance indices, based on the parameter change amount,
wherein the radar chart display generator is configured to generate and display the corresponding current performance index radar chart in the standard radar chart based on the performance index change amounts.

13. The apparatus as claimed in claim 11, wherein:
the standard radar chart normalizes the standard value of each of the performance indices to be a set value for display; and
the radar chart display generator is configured to:
when previewing the current sequence in the multiple predetermined sequences, normalize the reference value of each performance index in the multiple performance indices based on the sequence, based on the standard value of each of the performance indices and the set value;
when previewing the current sequence in the multiple predetermined sequences, display the corresponding reference performance index radar chart in the standard radar chart based on a normalized performance index value;
when previewing the current parameter of the current sequence, normalize the current values of the multiple performance indices based on the standard value of each of the performance indices and the set value, and when previewing the current parameter of the current sequence, generate and display the corresponding current performance index radar chart in the standard radar chart based on the normalized performance index value.

14. The apparatus as claimed in claim 11, further comprising:
a storage that stores the reference value of each performance index in the multiple performance indices obtained in advance based on the current sequence,
wherein the reference value of each performance index in the multiple performance indices comprises:
a maximum value of each performance index obtained by performing parameter adjustment based on the current sequence; or
a value of each performance index obtained based on a set of recommended parameters of the current sequence.

15. The apparatus as claimed in claim 11, wherein:
the storage further stores the standard value of each performance index obtained in advance based on at least one sequence; and
the standard value of each performance index comprises:
a maximum value of each performance index obtained by performing parameter adjustment based on a single sequence;
a value of each performance index obtained based on a set of recommended parameters of a single sequence; or
a maximum value of each performance index obtained by performing parameter adjustment based on multiple sequences.

16. The apparatus as claimed in claim 11, wherein:
the storage further stores an advance warning value of each performance index; and
when previewing the current parameter of the current sequence, the radar chart display generator is further configured to display a corresponding advance warning performance index radar chart in the standard radar chart based on the advance warning value of each of the performance indices.

17. The apparatus as claimed in claim 11, wherein:
the storage further stores:
a default recommended parameter, corresponding to each scanning region, which is set in advance for each sequence in the multiple sequences, and
a recommended value of each performance index obtained to correspond to the recommended parameter, the recommended parameter enabling each performance index to attain a set balance on the basis of the current sequence; and
when previewing the current parameter of the current sequence, the radar chart display generator is further configured to display a corresponding recommended performance index radar chart in the standard radar chart based on the recommended value of each of the performance indices.

18. A magnetic resonance imaging (MRI) system, comprising:
an MRI scanner; and
the protocol parameter selection apparatus as claimed in claim 2.

* * * * *